US011414363B2

(12) United States Patent
Pretz et al.

(10) Patent No.: US 11,414,363 B2
(45) Date of Patent: Aug. 16, 2022

(54) CHEMICAL PROCESSING UTILIZING HYDROGEN CONTAINING SUPPLEMENTAL FUEL FOR CATALYST PROCESSING

(71) Applicant: Dow Global Technologies LLC, Midland, MI (US)

(72) Inventors: Matthew T. Pretz, Lake Jackson, TX (US); Mark W. Stewart, Pearland, TX (US); Lin Luo, Sugarland, TX (US); Hangyao Wang, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/256,706

(22) PCT Filed: Jun. 26, 2019

(86) PCT No.: PCT/US2019/039209
§ 371 (c)(1),
(2) Date: Dec. 29, 2020

(87) PCT Pub. No.: WO2020/009860
PCT Pub. Date: Jan. 9, 2020

(65) Prior Publication Data
US 2021/0261482 A1    Aug. 26, 2021

Related U.S. Application Data

(60) Provisional application No. 62/694,193, filed on Jul. 5, 2018.

(51) Int. Cl.
*C07C 5/333*    (2006.01)
*B01J 8/00*    (2006.01)
(Continued)

(52) U.S. Cl.
CPC ............ *C07C 5/3337* (2013.01); *B01J 8/0035* (2013.01); *B01J 8/1827* (2013.01); *B01J 8/1845* (2013.01);
(Continued)

(58) Field of Classification Search
CPC ......... C07C 5/3337; C07C 5/32; C07C 5/325; C07C 5/327; C07C 2521/04;
(Continued)

(56) References Cited

U.S. PATENT DOCUMENTS

| 4,072,600 A | 2/1978 | Schwartz |
| 7,595,427 B2 * | 9/2009 | Sanfilippo .............. B01J 8/0055 585/444 |

(Continued)

FOREIGN PATENT DOCUMENTS

| EP | 637578 A1 | 2/1995 |
| WO | 0156960 A1 | 8/2001 |

(Continued)

OTHER PUBLICATIONS

Deutschmann, et al., Hydrogen assisted catalytic combustion of methane on platinum; Catalysis Today, 2000, 59(1-2), 141-150.

(Continued)

*Primary Examiner* — Ali Z Fadhel
(74) *Attorney, Agent, or Firm* — Dinsmore & Shohl LLP

(57) ABSTRACT

A method for processing a chemical stream includes contacting a feed stream with a catalyst in a reactor portion of a reactor system that includes a reactor portion and a catalyst processing portion. The catalyst includes platinum, gallium, or both and contacting the feed stream with the catalyst causes a reaction which forms an effluent stream. The method includes separating the effluent stream from the catalyst, passing the catalyst to the catalyst processing portion, and processing the catalyst in the catalyst process- (Continued)

ing portion. Processing the catalyst includes passing the catalyst to a combustor, combusting a supplemental fuel in the combustor to heat the catalyst, treating the heated catalyst with an oxygen-containing gas to produce a reactivated catalyst, and passing the reactivated catalyst from the catalyst processing portion to the reactor portion. The supplemental fuel may include a molar ratio of hydrogen to other combustible fuels of at least 1:1.

20 Claims, 6 Drawing Sheets

(51) Int. Cl.
| | |
|---|---|
| B01J 8/18 | (2006.01) |
| B01J 8/24 | (2006.01) |
| B01J 21/12 | (2006.01) |
| B01J 23/62 | (2006.01) |
| B01J 23/96 | (2006.01) |
| B01J 38/02 | (2006.01) |
| B01J 38/12 | (2006.01) |
| C07C 5/32 | (2006.01) |
| C07C 5/327 | (2006.01) |

(52) U.S. Cl.
CPC .............. *B01J 8/24* (2013.01); *B01J 21/12* (2013.01); *B01J 23/62* (2013.01); *B01J 23/96* (2013.01); *B01J 38/02* (2013.01); *B01J 38/12* (2013.01); *B01J 2208/00769* (2013.01); *C07C 5/32* (2013.01); *C07C 5/325* (2013.01); *C07C 5/327* (2013.01); *C07C 2521/04* (2013.01); *C07C 2521/08* (2013.01); *C07C 2523/08* (2013.01); *C07C 2523/42* (2013.01); *C07C 2523/62* (2013.01)

(58) Field of Classification Search
CPC ............ C07C 2521/08; C07C 2523/08; C07C 2523/42; C07C 2523/62; C07C 11/06; B01J 8/0035; B01J 8/1827; B01J 8/1845; B01J 8/24; B01J 21/12; B01J 23/62; B01J 23/96; B01J 38/02; B01J 38/12; B01J 2208/00769; Y02P 20/52; Y02P 20/584

See application file for complete search history.

(56) References Cited

U.S. PATENT DOCUMENTS

| | | | |
|---|---|---|---|
| 8,669,406 | B2 | 3/2014 | Pretz et al. |
| 9,815,040 | B2 | 11/2017 | Pretz et al. |
| 9,827,543 | B2 | 11/2017 | Pretz et al. |
| 9,834,496 | B2 | 12/2017 | Pretz et al. |
| 10,065,905 | B2 | 9/2018 | Pretz et al. |
| 2004/0029715 | A1 | 2/2004 | Schindler et al. |
| 2004/0259727 | A1* | 12/2004 | Bartolini ............... C07C 5/3332 502/324 |
| 2010/0004118 | A1 | 1/2010 | Liu et al. |
| 2010/0236985 | A1 | 9/2010 | Luo et al. |
| 2011/0269620 | A1* | 11/2011 | Myers ..................... B01J 38/10 502/56 |
| 2014/0200385 | A1 | 7/2014 | Pretz et al. |
| 2014/0378731 | A1* | 12/2014 | Iezzi ..................... C07C 5/3335 585/660 |
| 2016/0060542 | A1 | 3/2016 | Sugita et al. |
| 2016/0152901 | A1 | 6/2016 | Dufresne |
| 2017/0087528 | A1 | 3/2017 | Pretz et al. |

FOREIGN PATENT DOCUMENTS

| | | |
|---|---|---|
| WO | 02096844 A1 | 12/2002 |
| WO | 2005077867 A2 | 8/2005 |
| WO | 2010107591 A1 | 9/2010 |
| WO | 2013009820 A1 | 1/2013 |
| WO | 2016160273 A1 | 10/2016 |
| WO | 2017151361 A1 | 9/2017 |

OTHER PUBLICATIONS

Warnatz, et al., A model of elementary chemistry and fluid mechanics in the combustion of hydrogen on platinum surfaces; Combustion and Flame, (1994), 96(4), 393-406.
Rinnemo, et al., Experimental and numerical investigation of the catalytic ignition of mixtures of hydrogen and oxygen on platinum Combustion and Flame, (1977), 111(4), 312-326.
Tiernan, et al., Effects of ceria on the combustion activity and surface properties of Pt/Al2O3 catalysts; Applied Catalysis, B. Environmental, (1998), 19(1), 23-35.
Ikeda, et al., Surface kinetics for catalytic combustion of hydrogen-air mixtures on platinum at atmospheric pressure in stagnation flows; Surface Science, (1995), 326(1/2), 11-26.
Examination Report pertaining to corresponding G.C.C. Patent Application No. 2019-37879, dated Apr. 29, 2020.
Examination Report pertaining to corresponding G.C.C. Patent Application No. 2019-37879, dated Jul. 15, 2020.
International Search Report and Written Opinion pertaining to PCT/US2019/039209, dated Oct. 2, 2019.
International Search Report and Written Opinion pertaining to PCT/US2019/039212, dated Oct. 1, 2019.
International Search Report and Written Opinion pertaining to PCT/US2019/039216, dated Oct. 9, 2019.
U.S. Office Action dated Oct. 13, 2021 pertaining to U.S. Appl. No. 17/256,690, filed Dec. 29, 2020, 20 pages.
Sadeghbeigi, R., Fluid Catalytic Cracking Handbook, Third Edition, Chapter 10: pp. 197-219 (Year: 2012).
U.S. Office Action dated Mar. 18, 2022 pertaining to U.S. Appl. No. 17/256,690, filed Dec. 29, 2020, 12 pages.

* cited by examiner

CHEMICAL PROCESSING UTILIZING HYDROGEN CONTAINING SUPPLEMENTAL FUEL FOR CATALYST PROCESSING

CROSS-REFERENCE TO RELATED APPLICATIONS

This application is a National Stage Entry under 35 U.S.C. § 371 of International Patent Application No. PCT/US2019/039209, filed Jun. 26, 2019, which claims the benefit of U.S. Provisional Patent Application Ser. No. 62/694,193, filed Jul. 5, 2018, both of which are hereby incorporated by reference in their entireties.

BACKGROUND

Field

The present disclosure generally relates to chemical processing systems and the operation thereof and, more specifically, to processes including supplemental fuel streams for processing catalysts.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as a product stream from a crude oil refining operation. Many light olefins may be produced through various catalytic processes, such as through catalytic dehydrogenation for example, in which the feed stream is contacted with a fluidized catalyst that facilitates conversion of the feed stream into the light olefins.

BRIEF SUMMARY

Many reaction processes for producing light olefins are endothermic and require heat input into the system to propagate the catalytic reactions. Coke deposits on the catalyst may be combusted during catalyst regeneration, but the heat provided by combustion of coke deposits may not be sufficient to propagate the endothermic reactions. Supplemental fuels may be introduced during catalyst regeneration to increase the heat input into the reaction system.

There is a continued need for improved processes for reactor systems for processing chemical streams to produce light olefins or other chemical products, the processes including improved supplemental fuel sources for heating the catalyst. Many reactor systems for processing chemical streams to produce light olefins and other chemicals utilize relatively hot catalyst, such as those catalysts heated to temperatures greater than 350° C. The catalyst may be circulated through fluidized reactor systems, such as through a reactor portion (where chemical products are made) and through a catalyst processing portion (where the catalyst is processed, such as but not limited to removal of coke, heating of the catalyst, reactivating the catalyst, other catalyst processing operations, or combinations of these).

In endothermic fluidized reactor systems, the reactor system may include a heat source to drive the process. For example, in fluidized catalytic cracking ("FCC") reactions, coke generated by the reaction and deposited on the catalyst may be combusted in a combustor of the catalyst processing portion to provide a major portion of the heat to drive the reaction process. As another non-limiting example, in fluidized catalytic dehydrogenation (FCDh) reactions, a supplemental fuel may be added to the combustor to provide additional heat for the endothermic reaction along with combustion of a relatively small amount of coke generated from the dehydrogenation reaction. Supplemental fuels may include significant proportions of methane and/or other hydrocarbons due to the relatively inexpensive cost of methane and its energy efficiency at relatively high temperatures, such as those of the catalyst during operation of the reactor system (e.g., temperatures above 650° C.). However, combustion of supplemental fuels that include mainly methane and other hydrocarbons (e.g., greater than or equal to 50 mol % methane and other hydrocarbons) during catalyst processing may lead to reduced activity of the catalyst, such as a catalyst that includes platinum, gallium, or both for example.

The reduced activity of the catalysts can decrease the conversion that can be attained by the catalyst. In some fluidized reactor systems that utilize supplemental fuels that include mainly methane and other hydrocarbons, productivity of the reactor system may be maintained by increasing the amount of the catalyst in the reactor system or increasing the amount of active metal, such as platinum, gallium, or both, in the catalyst. However, increasing the amount of active metal, such as platinum, gallium, or both, in the reactor system can increase the operating costs of the reactor system.

Therefore, there is an ongoing need for reactor systems and processes that increase the conversion of a chemical feed by reducing deactivation of the catalyst. In particular, there is an ongoing need for reactor systems and methods that include combusting supplemental fuels that reduce the extent of deactivation of the catalysts during combustion of the supplemental fuel, thereby increasing catalyst activity. The present disclosure, according to one or more embodiments, is directed to processes and reactor systems that include combusting a supplemental fuel having a relatively high concentration of hydrogen (e.g., molar ratio of hydrogen to other combustible fuels of at least 1:1) in the combustor of a catalyst processing portion of the reactor system to heat the catalyst. Following combustion, the catalyst may be subjected to an oxygen treatment that includes exposing the catalyst to an oxygen-containing gas for a time sufficient to reactive the catalyst.

It was surprisingly and unexpectedly found that combusting a supplemental fuel having a relatively high concentration of hydrogen can result in greater catalyst activity and an increase in the conversion of the reactor system compared to the conventional case of combusting a supplemental fuel that includes relatively high amounts of hydrocarbons (e.g., methane) under the same operating conditions (including the same oxygen treatment following combustion). Additionally, combustion of supplemental fuels that include relatively high concentrations of hydrogen can result in a catalyst with longer catalyst lifetime and may enable a target conversion to be achieved with less bulk inventory of catalyst in the reactor system compared to the bulk inventory needed to achieve the same target conversion when the supplemental fuel is mainly hydrocarbons (e.g., >50 mol % hydrocarbons). In some embodiments, combusting a supplemental fuel having a high concentration of hydrogen may enable the reactor system to be operated with less active metal, such as platinum, gallium, or both, on the catalyst.

According to one or more aspects of the present disclosure, a method for processing a chemical stream may include contacting a feed stream with a catalyst in a reactor portion of a reactor system. The reactor system may include a reactor portion and a catalyst processing portion, and the catalyst may include platinum, gallium, or both. The contacting of the feed stream with the catalyst causes a reaction which forms an effluent stream comprising at least one product. The method may further include separating at least a portion of the effluent stream from the catalyst, passing the catalyst to the catalyst processing portion of the reactor system, and processing the catalyst in the catalyst processing portion of the reactor system. Processing the catalyst may include passing the catalyst to a combustor of the catalyst processing portion, combusting a supplemental fuel in the combustor in the presence of the catalyst to produce a heated catalyst, treating the heated catalyst with an oxygen-containing gas (oxygen treatment) to produce a reactivated catalyst, and passing the reactivated catalyst from the catalyst processing portion to the reactor portion. The supplemental fuel may include hydrogen and other combustible fuels, and a molar ratio of hydrogen to the other combustible fuels in the supplemental fuel is at least 1:1.

According to one or more other aspects of the present disclosure, a method for dehydrogenating a hydrocarbon to produce one or more olefins may include contacting the hydrocarbon feed stream with a catalyst in a reactor portion of a reactor system. The reactor system may include a reactor portion and a catalyst processing portion, and the catalyst may include platinum, gallium, or both. The contacting of the feed stream with the catalyst may cause a reaction which forms an effluent stream comprising at least one product. The method may further include separating at least a portion of the effluent stream from the catalyst, passing the catalyst to the catalyst processing portion of the reactor system, and processing the catalyst in the catalyst processing portion of the reactor system. Processing the catalyst may include passing the catalyst to a combustor of the catalyst processing portion, introducing a supplemental fuel to the combustor, combusting the supplemental fuel in the combustor in the presence of the catalyst, subjecting a heated catalyst to an oxygen treatment to produce a reactivated catalyst, and passing the reactivated catalyst from the catalyst processing portion to the reactor portion. The supplemental fuel stream may include hydrogen and at least one hydrocarbon, and a molar ratio of hydrogen to other combustible fuels in the supplemental fuel is at least 1:1.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
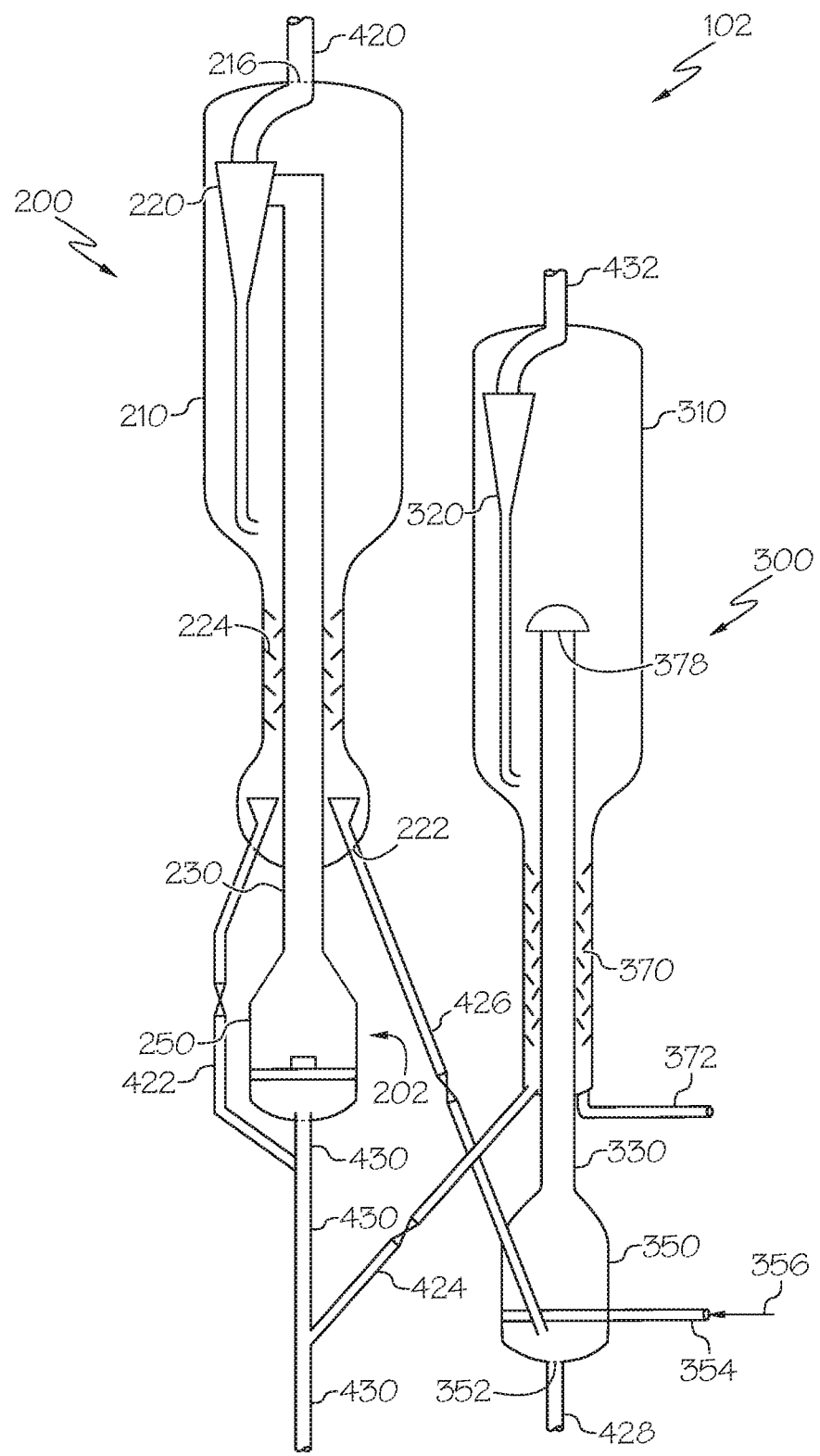
FIG. 1 schematically depicts a reactor system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Several embodiments of the present disclosure are discussed in the detailed description which follows. One or more embodiments of the present disclosure are directed to methods for processing chemical streams in reactor systems utilizing a supplemental fuel to heat a catalyst. In particular, one or more embodiments of the present disclosure are directed to methods for processing chemical streams in which a supplemental fuel that includes hydrogen is combusted in a catalyst processing portion of the reactor system to heat the catalyst. For example, in some embodiments, the method for processing a chemical stream may include contacting a feed stream with a catalyst in a reactor portion of a reactor system that includes a reactor portion and a catalyst processing portion. The catalyst may include platinum, gallium, or both. Contacting of the feed stream with the catalyst may cause a reaction which forms an effluent stream that contains at least one product, such as an olefin product for example. The method may include separating at least a portion of the effluent stream from the catalyst and passing the catalyst to the catalyst processing portion of the reactor system. The method may further include processing the catalyst in the catalyst processing portion. Processing the catalyst may include passing the catalyst to a combustor of the catalyst processing portion and combusting a supplemental fuel that includes a high-concentration of hydrogen (molar ratio of hydrogen to other combustible fuels of at least 1:1) in the combustor. Combusting the supplemental fuel that includes a relatively high concentration of hydrogen may increase the temperature of the catalyst to produce a heated catalyst. Processing the catalyst may also include treating the heated catalyst with an oxygen-containing gas to produce a reactivated catalyst. The reactivated catalyst may be passed back to the reactor portion of the reactor system.

Combustion of the supplemental fuel that includes a relatively high concentration of hydrogen (e.g., molar ratio of hydrogen to other combustible fuels of at least 1:1) to heat the catalyst during catalyst processing was found to increase the conversion of reactants in the reactor system compared to combusting a supplemental fuel consisting mainly of methane or other hydrocarbons. This high activity may result in increased catalyst lifetime in the reactor system and may enable increasing the unit capacity of the reactor system. The higher catalyst activity may also enable the reactor system to operate with less active metal, such as platinum, gallium, or both, in the reactor system (e.g., less bulk inventory of catalyst or less active metal in the catalyst).

As used herein, the term "fluidized reactor system" refers to a reactor system in which one or more reactants are contacted with a catalyst in a fluidization regime, such as bubbling regime, slug flow regime, turbulent regime, fast fluidization regime, pneumatic conveying regime, or combinations thereof in different portions of the system. For example, in a fluidized reactor system, a feed stream containing one or more reactants may be contacted with the circulating catalyst at an operating temperature to conduct a continuous reaction to produce the product stream.

As used herein, "continuous reaction" may refer to a chemical reaction conducted by feeding reactants, catalyst, or combinations thereof, and withdrawing products from a reactor or reaction zone under steady state conditions continuously over a time period, which is defined by a commencement of the reaction at the beginning of the time period and a cessation of the reaction at the end of the time period. Thus, operation of the reactor systems described herein may include commencement of the reaction, continuous reaction, and cessation of the reaction.

As used herein, "deactivated catalyst" may refer to a catalyst having decreased catalytic activity resulting from buildup of coke and/or loss of catalyst active sites.

As used herein, "catalytic activity" or "catalyst activity" may refer to the degree to which the catalyst is able to catalyze the reactions conducted in the reactor system.

As used herein, "catalyst processing" may refer to preparing the catalyst for re-introduction into the reactor portion of the reactor system and may include removing coke deposits from the catalyst, heating the catalyst, reactivating the catalyst, stripping one or more gases from the catalyst, other processing operations, or any combinations of these.

As used herein, "processed catalyst" may refer to catalyst that has been processed in the catalyst processing portion of the reactor system.

As used herein, "catalyst reactivation" or "reactivating the catalyst" may refer to processing the deactivated catalyst to restore at least a portion of the catalyst activity to produce a reactivated catalyst. The deactivated catalyst may be reactivated by, but not limited to, recovering catalyst acidity, oxidizing the catalyst, other reactivation process, or combinations thereof. In some embodiments, catalyst reactivation may include treating the catalyst with an oxygen-containing gas for a period of greater than 2 minutes.

As used herein, "supplemental fuel" may refer to any fuel source introduced to the catalyst processing portion of the reactor system to facilitate removing coke from the catalyst and/or heating the catalyst. Supplemental fuel does not include coke deposited on the catalyst.

As previously discussed herein, according to one or more embodiments, the methods and processes disclosed herein may be utilized to conduct a reaction in a reactor system for processing one or more chemical streams. In non-limiting examples, the reactor systems disclosed herein may be utilized to produce light olefins from hydrocarbon feed streams through continuous reaction of the hydrocarbon feed streams. For example, in some embodiments, light olefins may be produced through dehydrogenation of a hydrocarbon feed stream in the presence of a catalyst that includes platinum, gallium, or both in a fluidized catalytic dehydrogenation (FCDh) reactor system. While the processes and methods for processing a chemical stream in a reactor system are described herein in the context of hydrocarbon processing to form light olefins through fluidized catalytic dehydrogenation, it should be understood that the processes and methods disclosed herein may be utilized with any reactor system that includes a catalyst having an active metal, such as platinum, gallium, other active metal, or combinations thereof, and that includes heating the catalyst by combustion of a supplemental fuel. As such, the presently described methods and processes for processing a chemical stream in a reactor system should not be limited only to embodiments for reactor systems designed to produce light olefins or alkyl aromatics through fluidized catalytic dehydrogenation, such as the reactor system in FIG. 1.

The reactor systems and methods for processing the chemical streams will now be discussed in further detail. The chemical stream that is processed may be referred to as a feed stream, which is processed by a reaction to form a product stream. The feed stream may comprise a composition, and depending upon the feed stream composition, an appropriate catalyst may be utilized to convert the contents of the feed stream into a product stream that may include light olefins or other chemical products. For example, a feed stream for an FCDh reactor system may comprise at least one of propane, n-butane, iso-butane, ethane, or ethylbenzene. In the FCDh system, the feed stream may be converted to light olefins or other products through dehydrogenation in the presence of a dehydrogenation catalyst.

In some embodiments, the catalyst for conducting dehydrogenation in an FCDh reactor system may include a catalyst comprising platinum, gallium, or both. In some embodiments, the catalyst may further include one or more other noble metals from Groups 9 and 10 of the IUPAC periodic table. For example, in some embodiments, the catalyst may include one or more noble metals chosen from, palladium (Pd), rhenium (Rh), iridium (Jr), or combinations of these. In some embodiments, the catalyst may also include one or more metals chosen from indium (In), germanium (Ge), or combinations of these. The catalyst may also include a promoter metal, such as an alkali metal or an alkaline metal. In some embodiments, the promoter metal may be potassium. The metals of the catalyst may be supported on a carrier. The carrier may include one or more inorganic bulk metal oxides, such as silica, alumina, alumina-containing silica, zirconia ($ZrO_2$), titania ($TiO_2$), other metal oxides, or combinations of metal oxides. In some embodiments, the carrier may include a microporous material, such as ZSM-5 zeolite. The catalytic metals, such as platinum, gallium, potassium, and/or other catalytically active metals, may be supported on the surface of the carrier or incorporated into the carrier. In some embodiments, the catalyst may include platinum, gallium, and optionally potassium supported on an alumina-containing silica carrier.

Referring now to FIG. 1, an example reactor system 102 is schematically depicted. The reactor system 102 generally includes a reactor portion 200 and a catalyst processing portion 300. As used herein in the context of FIG. 1, the reactor portion 200 refers to the portion of a reactor system 102 in which the major process reaction takes place. For example, the reactor system 102 may be an FCDh system in which the feed stream is dehydrogenated in the presence of the dehydrogenation catalyst in the reactor portion 200 of the reactor system 102. The reactor portion 200 comprises a reactor 202 which may include a downstream reactor section 230, an upstream reactor section 250, and a catalyst separation section 210, which serves to separate the catalyst from the chemical products formed in the reactor 202.

Also, as used herein, the catalyst processing portion 300 of the system of FIG. 1 generally refers to the portion of a reactor system 102 in which the catalyst is in some way processed, such as removal of coke deposits, heating of the catalyst, reactivating the catalyst, other processing operations, or combinations of these. In some embodiments, the catalyst processing portion 300 may include a combustor 350, a riser 330, a catalyst separation section 310, and an oxygen treatment zone 370. The combustor 350 of the catalyst processing portion 300 may include one or more lower combustor inlet ports 352 and may be in fluid communication with the riser 330. The combustor 350 may be in fluid communication with the catalyst separation section 210 via standpipe 426, which may supply deactivated catalyst from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via standpipe 424 and transport riser 430), which may supply processed catalyst from the catalyst processing portion 300 back to the reactor portion 200. The combustor 350 may include the lower combustor inlet port 352 where air inlet 428 connects to the combustor 350. The air inlet 428 may supply air or other reactive gases, such as an oxygen-containing gas to the combustor 350. Air and/or other reactive gases, may be introduced to the combustor 350 to aid in combustion of the supplemental fuel. The combustor 350 may also include a supplemental fuel inlet 354. The supplemental fuel inlet 354 may supply a supplemental fuel stream 356 to the combustor 350. The supplemental fuel stream 356 may include the supplemental fuel. The oxygen treatment zone 370 may include an oxygen-containing gas inlet 372, which may supply an oxygen-containing gas to the oxygen treatment zone 370 for oxygen treatment of the catalyst.

Referring to FIG. 1, general operation of the reactor system 102 to conduct a continuous reaction will be described. During operation of the reactor portion 200 of the reactor system 102, the feed stream may enter the transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed may contact the catalyst in the upstream reactor section 250, and each may flow upwardly into and through the downstream reactor section 230 to produce a chemical product. The chemical product and the catalyst may be passed out of the downstream reactor section 230 to a separation device 220 in the catalyst separation section 210. The catalyst may be separated from the chemical product in the separation device 220. The chemical product may then be transported out of the catalyst separation section 210. For example, the separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation.

According to some embodiments, following separation from vapors in the separation device 220, the catalyst may generally move through the stripper 224 to the reactor catalyst outlet port 222 where the catalyst may be transferred out of the reactor portion 200 via standpipe 426 and into the catalyst processing portion 300. Optionally, the catalyst may also be transferred directly back into the upstream reactor section 250 via standpipe 422. In some embodiments, recycled catalyst from the stripper 224 may be premixed with processed catalyst from the catalyst processing portion 300 in the transport riser 430.

The separated catalyst may be passed from the catalyst separation section 210 to the combustor 350 of the catalyst processing portion 300. The catalyst may be processed in the catalyst processing portion 300 to remove coke deposits, heat the catalyst, reactivate the catalyst, other catalyst processing, or any combinations of these. As previously discussed, processing the catalyst in the catalyst processing portion 300 may include removing coke deposits from the catalyst, raising the temperature of the catalyst through combustion of a combustion fuel source, reactivating the catalyst, stripping one or more constituents from the catalyst, other processing operation, or combinations of these. In some embodiments, processing the catalyst in the processing portion 300 may include combusting a combustion fuel source in the presence of the catalyst in the combustor 350 to remove coke deposits and/or heat the catalyst to produce a heated catalyst. The heated catalyst may be separated from the combustion gases in the catalyst separation portion 310. In some embodiments, the heated catalyst may then be reactivated by conducting an oxygen treatment of the heated catalyst. The oxygen treatment may include exposing the catalyst to an oxygen-containing gas for a period of time sufficient to reactivate the catalyst.

In some embodiments, the combustion fuel source may include coke or other contaminants deposited on the catalyst in the reactor portion 200 of the reactor system 102. In some reaction systems, the catalyst may be coked following the reactions in the reactor portion 200, and the coke may be removed from the catalyst by a combustion reaction in the combustor 350. For example, oxidizer (such as air) may be fed into the combustor 350 via the air inlet 428.

However, as previously discussed, in some reaction systems, the coke and other contaminants deposited on the catalyst may not be sufficient to heat the catalyst to a temperature great enough to carry out the endothermic reactions in the reactor portion 200. Thus, the combustion fuel source may further include a supplemental fuel. The supplemental fuel may be part of the supplemental fuel stream 356, which may be introduced to the combustor 350 through a supplemental fuel inlet 354. For example, the supplemental fuel stream 356 may be injected into the combustor 350 through the supplemental fuel inlet 354 and the supplemental fuel combusted to heat the catalyst to a temperature sufficient to conduct the endothermic reactions in the reactor portion 200 as well provide for the other heat demands in the entire reactor system 102. In some embodiments, no coke may be formed on the catalyst such that all of the heat for raising the temperature of the catalyst is provided by the supplemental fuel. In some embodiments, reactive gases, such as an oxygen-containing gas (e.g., air) or other oxidizer for example, may be introduced to the combustor 350 through lower combustor inlet port 352 and may react with the supplemental fuel of the supplemental fuel stream 356 to promote combustion of the supplemental fuel to heat the catalyst to produce the heated catalyst. As used herein, the term "heated catalyst" refers to the catalyst after heating through combustion of the supplemental fuel stream 356, the catalyst having a temperature greater than the catalyst passed from the catalyst separation section 210 to the catalyst processing portion 300 of the reactor system 102.

Referring to FIG. 1, the processed catalyst may be passed out of the combustor 350 and through the riser 330 to a riser termination separator 378, where the gas and solid components from the riser 330 may be at least partially separated. The vapor and remaining solids may be transported to a secondary separation device 320 in the catalyst separation section 310 where the remaining processed catalyst is separated from the gases from the catalyst processing (e.g., gases emitted by combustion of coke deposits and supplemental fuel). In some embodiments, the secondary separation device 320 may include one or a plurality of cyclone separation units, which may be arranged in series or in multiple cyclone pairs. The combustion gases from combustion of coke and/or the supplemental fuel during processing of the catalyst or other gases introduced to the catalyst during catalyst processing may be removed from the catalyst processing portion 300 via a combustion gas outlet 432.

As previously discussed, processing the catalyst in the catalyst processing portion 300 of the reactor system 102 may include reactivating the catalyst. Combustion of the supplemental fuel in the presence of the catalyst to heat the catalyst may further deactivate the catalyst. Thus, in some embodiments, the catalyst may be reactivated by conditioning the catalyst through an oxygen treatment. The oxygen treatment to reactivate the catalyst may be conducted after combustion of the supplemental fuel to heat the catalyst. The oxygen treatment may include treating the heated catalyst with an oxygen-containing gas for a period of at least two minutes, which may reactivate the catalyst to produce a reactivated catalyst. The oxygen-containing gas may include an oxygen content of from 5 mole % to 100 mole % based on total molar flow rate of the oxygen-containing gas. In some embodiments, the catalyst may be reactivated by conditioning the catalyst through an oxygen treatment. Oxygen treatment of the catalyst may include maintaining the catalyst at a temperature of at least 660° C. while exposing the catalyst to a flow of an oxygen-containing gas for a period of time greater than two minutes and sufficient to produce a reactivated catalyst having a catalytic activity that is greater than the heated catalyst after being heated by combustion of the supplemental fuel.

Referring to FIG. 1, treatment of the heated catalyst with the oxygen-containing gas may be conducted in the oxygen treatment zone 370. In some embodiments, the oxygen treatment zone 370 may be downstream of the catalyst separation portion 310 of the catalyst processing portion 300, such that the heated catalyst is separated from the combustion gases before being exposed to the oxygen-containing gas during the oxygen treatment. In some embodiments, the oxygen treatment zone 370 may include a fluid solids contacting device. The fluid solids contacting device may include baffles or grid structures to facilitate contact of the heated catalyst with the oxygen-containing gas. Examples of fluid solid contacting devices are described in further detail in U.S. Pat. Nos. 9,827,543 and 9,815,040, both of which are incorporated by reference herein in their entirety.

In some embodiments, processing the catalyst in the catalyst processing portion 300 of the reactor system 102 may further include stripping the oxygen-containing reactivated catalyst of molecular oxygen trapped within or between catalyst particles and physisorbed oxygen that is desorbable at a temperature of at least 660° C. The stripping step may include maintaining the oxygen-containing reactivated catalyst at a temperature of at least 660° C. and exposing the oxygen-containing reactivated catalyst to a stripping gas that is substantially free of molecular oxygen and combustible fuels for a period of time to remove the molecular oxygen from between particles and physisorbed oxygen that is desorbable at the temperature of at least 660° C. Further description of these catalyst reactivation processes are disclosed in U.S. Pat. No. 9,834,496, which is incorporated by reference in the present disclosure in its entirety.

Following processing of the catalyst, the processed catalyst may be passed from the catalyst processing portion 300 back into the reactor portion 200 via standpipe 424. For example, in some embodiments, the processed catalyst may be passed from the oxygen treatment zone 370 of the catalyst processing portion 300 to the upstream reactor section 250 via standpipe 424 and transport riser 430, where the processed catalyst may be further utilized in a catalytic reaction. Thus, in operation, the catalyst may cycle between the reactor portion 200 and the catalyst processing portion 300. In general, the processed chemical streams, including the feed streams and product streams may be gaseous, and the catalyst may be a fluidized particulate solid.

Referring again to FIG. 1, according to one or more embodiments, processing the catalyst in the catalyst processing portion 300 may include passing the catalyst from the reactor portion 200 of the reactor system 102 to the combustor 350 of the catalyst processing portion 300, combusting the supplemental fuel in the combustor 350 to heat the catalyst, subjecting the heated catalyst to an oxygen treatment in the oxygen treatment zone 370 to produce a reactivated catalyst, and passing the reactivated catalyst from catalyst processing portion 300 to the reactor portion 200. Combustion of the supplemental fuel and/or coke deposits in the catalyst processing portion 300 may remove the coke deposits or other contaminants deposited on the catalyst, increase the temperature of the catalyst to an operating temperature range of the reactor portion 200, or both. For example, in some embodiments, combustion of the supplemental fuel in the combustor 350 may increase the temperature of the catalyst to produce a heated catalyst. In some embodiments, coke deposits may not be formed on the catalyst during the reaction, and the supplemental fuel may provide all of the heat in the combustor for raising the temperature of the catalyst to produce the heated catalyst.

In some embodiments, the supplemental fuel may include hydrogen and other combustible fuels. A molar ratio of hydrogen to the other combustible fuels in the supplemental fuel may be at least 1:1. For example, in some embodiments, the molar ratio of hydrogen to other combustible fuels in the supplemental fuel may be greater than or equal to 7:3, greater than or equal to 4:1, or even greater than or equal to 9:1. In some embodiments, the molar ratio of hydrogen to other combustible fuels in the supplemental fuel may be from 1:1 to 999:1, from 1:1 to 99:1, from 1:1 to 49:1, from 1:1 to 19:1, from 1:1 to 9:1, from 7:3 to 999:1, from 7:3 to 99:1, from 7:3 to 49:1, from 7:3 to 19:1, from 7:3 to 9:1, from 4:1 to 999:1, from 4:1 to 99:1, from 4:1 to 49:1, from 4:1 to 19:1, or from 4:1 to 9:1.

In some embodiments, the supplemental fuel may include greater than or equal to 70 mol % hydrogen, such as greater than or equal to 75 mol %, greater than or equal to 80 mol %, greater than or equal to 85 mol %, or greater than or equal to 90 mol % hydrogen, based on the total moles of combustible constituents in the supplemental fuel. Combustible constituents can include the hydrogen, hydrocarbons, and other combustible fuels, or any other constituent that undergoes combustion at temperatures in the operating range of the combustor 350, but does not include constituents, such as inert gases (e.g., nitrogen, argon, etc.) and other constituents that do not combust at temperatures in the operating range of the combustor 350. For example, in some embodiments, the supplemental fuel may include from 70 mol % to 100 mol %, from 70 mol % to 99 mol %, from 70 mol % to 95 mol %, from 70 mol % to 90 mol %, from 70 mol % to 85 mol %, from 75 mol % to 100 mol %, from 75 mol % to 99 mol %, from 75 mol % to 95 mol %, from 75 mol % to 90 mol %, from 75 mol % to 85 mol %, from 80 mol % to 100 mol %, from 80 mol % to 99 mol %, from 80 mol % to 95 mol %, from 80 mol % to 90 mol %, from 85 mol % to 100 mol %, from 85 mol % to 99 mol %, from 85 mol % to 95 mol %, or from 90 mol % to 100 mol % hydrogen based on the total moles of combustible constituents in the supplemental fuel. The proportion of hydrogen in the supplemental fuel may also be expressed as a weight percent (wt. %). For example, in some embodiments, the supplemental fuel may include greater than or equal to 20 wt. %, greater than or equal to 25 wt. %, or greater than or equal to 30 wt. %, greater than or equal to 40 wt. %, or greater than or equal to 50 wt. % hydrogen based on the total mass of combustible constituents in the supplemental fuel. For example, in some embodiments, the supplemental fuel may include from 20 wt. % to 100 wt. %, from 20 wt. % to 99 wt. %, from 20 wt. % to 95 wt. %, from 25 wt. % to 100 wt. %, from 25 wt. % to 99 wt. %, from 25 wt. % to 95 wt. %, from 30 wt. % to 100 wt. %, from 30 wt. % to 99 wt. %, from 30 wt. % to 95 wt. %, from 40 wt. % to 100 wt. %, from 40 wt. % to 99 wt. %, from 40 wt. % to 95 wt. %, from 50 wt. % to 100 wt. %, or from 50 wt. % to 99 wt. % hydrogen based on the total mass of combustible constituents in the supplemental fuel.

It was surprisingly found that heating the catalyst with a supplemental fuel having a relatively high concentration of hydrogen (e.g., molar ratio of hydrogen to other combustible fuels of at least 1:1) can increase the conversion of the reactor system compared to reactivating the catalyst with a supplemental fuel that consists of mainly methane and other hydrocarbons (>50 mol % methane and/or other hydrocarbons). Incorporating a relatively high concentration of hydrogen into the supplemental fuel in combination with the oxygen treatment to reactivate the catalyst may result in a greater catalytic activity of the reactivated catalyst compared to catalyst heated by combustion of a supplemental fuel that consists of mainly methane and other hydrocarbons in combination with the oxygen treatment. As previously discussed, combustion of the supplemental fuel that includes a relatively high concentration of hydrogen to heat the catalyst in combination with the oxygen treatment may increase the lifetime of the catalyst in the reactor system 102. Further, combustion of the supplemental fuel having a relatively high concentration of hydrogen in combination with the oxygen treatment may also increase the capacity of the reactor system 102, such as by increasing the conversion for a specific catalyst loading or reducing the catalyst loading required to achieve a target conversion for example, compared to combusting a supplemental fuel with a high hydrocarbon concentration (>50 mol % hydrocarbon) to heat the catalyst. For example, in a reactor system 102 utilizing a catalyst comprising platinum, gallium, or both to dehydrogenate propane to produce propylene, operating the reactor system 102 utilizing a supplemental fuel having a molar ratio of hydrogen to other combustible fuels of at least 1:1 can produce the same conversion performance with less active metal (e.g., platinum, gallium, or both) compared to operating the reactor system with a supplemental fuel that is primarily methane and other hydrocarbons (i.e., >50 mol % hydrocarbon). Operating the reactor system with less active metal (e.g., platinum, gallium, or both) may include operating with a reduced bulk inventory of catalyst in the reactor system or reducing the amount of the active metal in the catalyst (e.g., using a catalyst having less active metal applied to the catalyst or using aged catalyst).

In some embodiments, the supplemental fuel may include other combustible fuels. Examples of other combustible fuels may include one or more hydrocarbons. The hydrocarbon may include a hydrocarbon or mixture of hydrocarbons that comprises energy value upon combustion. In some embodiments, the hydrocarbons may include one or more hydrocarbons that are gases at the operating temperatures of the combustor 350 (i.e., 650° C. to 850° C.), such as but not limited to, alkanes, alkenes, aromatic hydrocarbons, or combinations of these. Examples of alkanes that may be included as a hydrocarbon in the supplemental fuel may include, but are not limited to methane, ethane, propane, butane, isobutane, pentane, other alkanes, or combinations of these. Examples of alkenes (olefins) that may be included as a hydrocarbon of the supplemental fuel may include, but are not limited to, ethylene, propylene, 1-butene, 2-butene, isobutene, other olefins, or combinations of these. Examples of aromatic hydrocarbons that may be included as a hydrocarbon in the supplemental fuel may include, but are not limited to, benzene, toluene, xylene, other aromatic hydrocarbons, or combinations of these. In some embodiments, the hydrocarbons may include a light hydrocarbon (i.e., $C_1$-$C_4$) fuel gas. In other embodiments, the hydrocarbons may include heavy hydrocarbon based fuel oils ($C_{5+}$). In some embodiments, the hydrocarbon in the supplemental fuel may include at least one of methane, ethane, propane, natural gas, other hydrocarbon fuel, or combinations of these. Other combustible fuels other than hydrocarbons may also be included in the supplemental fuel.

In some embodiments, the supplemental fuel may include less than 30 mol % hydrocarbon based on the total moles of combustible constituents in the supplemental fuel. For example, in some embodiments, the supplemental fuel may include less than 25 mol %, less than 20 mol %, less than 15 mol %, or even less than 10 mol % hydrocarbon based on the total moles of combustible constituents in the supplemental fuel. Some hydrocarbon-based combustible fuels, such as methane and natural gas for example, have a high heat value and are relatively inexpensive. Thus, in some embodiments, hydrocarbon fuels, such as methane and natural gas for example, may be included in the supplemental fuel to reduce the operating costs of the reactor system 102. In other embodiments, the hydrocarbons in the supplemental fuel may be provided by an off-gas stream passed to the combustor 350 as at least a portion of the supplemental fuel stream 356, the off-gas stream originating from a hydrocarbon processing system. In some embodiments, the supplemental fuel stream 356 may include other non-combustible constituents. In some embodiments, the supplemental fuel stream 356 may include at least 10 mol % combustible constituents based on the total moles of the supplemental fuel. For example, the supplemental fuel stream 356 may include at least 20 mol %, at least 30 mol %, at least 40 mol %, at least 50 mol %, at least 70 mol %, at least 80 mol %, or at least 90 mol % combustible constituents based on the total moles of the supplemental fuel stream 356.

As previously discussed, the supplemental fuel stream 356 may include the supplemental fuel comprising hydrogen and other combustible fuels. In some embodiments, the supplemental fuel stream 356 may include a purity hydrogen stream comprising greater than or equal to 99 mol % hydrogen based on the total molar flow rate of the purity hydrogen stream. In some embodiments, the supplemental fuel stream 356 may include an off-gas stream from a hydrocarbon processing plant. The off-gas stream from a hydrocarbon processing plant/system may include greater than or equal to 50 mol %, greater than or equal to 60 mol %, greater than or equal to 70 mol %, greater than or equal to 80 mol %, or greater than or equal to 90 mol % hydrogen based on the total molar flow rate of combustible constituents in the off-gas stream. For example, in some embodiments, the supplemental fuel stream 356 may include an off-gas stream from an FCDh reactor system, such as but not limited to a propane dehydrogenation process, and/or an off-gas stream from a light hydrocarbon cracking process. It is understood that hydrogen-containing off-gas streams from other hydrocarbon processing systems may be included in the supplemental fuel stream 356. In some embodiments, the supplemental fuel stream 356 may consist of or consist essentially of an off-gas stream from a hydrocarbon processing system. In other embodiments, the supplemental fuel stream 356 may include the off-gas stream in combination with one or more other combustible fuel streams comprising hydrogen, a hydrocarbon component, other combustible fuel, or combinations of these. In some embodiments, the supplemental fuel stream 356 may include one or more inert constituents as a diluent. Examples of inert constituents may include inert gases such as nitrogen and argon for example, or other constituents that do not combust at temperatures in the operating range of the combustor 350.

Figure 2:
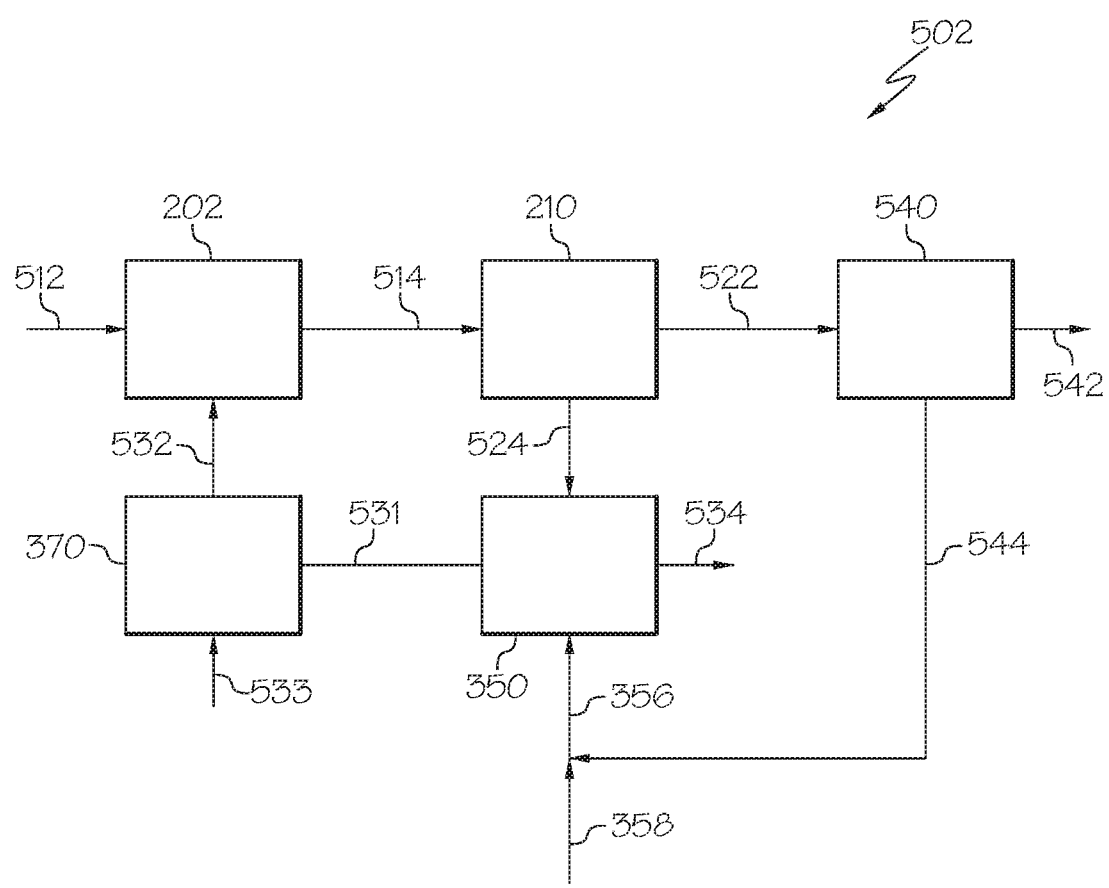
FIG. 2 schematically depicts a reactor system flow chart, according to one or more embodiments described herein.

Referring now to FIG. 2, a process flowchart of a fluidized catalytic dehydrogenation (FCDh) process 502 for dehydrogenating hydrocarbons to produce olefins and other products (e.g., styrene from ethylbenzene). In the FCDh process 502 of FIG. 2, an off-gas stream 544 recovered from the FCDh process 502 may be passed to the combustor 350 to provide at least a portion of the supplemental fuel stream 356. The FCDh process 502 depicted in FIG. 2 may include the reactor system 102 depicted in FIG. 1. The FCDh process 502 may include the reactor 202, the catalyst separation section 210, the combustor 350, and the oxygen treatment zone 370. The FCDh process 502 may further include a product separator 540 downstream of the catalyst separation section 210.

During continuous operation of the FCDh process 502 of FIG. 2, a chemical feed 512 and the reactivated catalyst 532 from the oxygen treatment zone 370 may be introduced to the reactor 202. Contact of reactants in the chemical feed 512 with the reactivated catalyst 532 may convert a portion of reactants in the chemical feed 512 to one or more reaction products (e.g., ethylene, propylene, styrene, etc.) and by-products. A reactor effluent 514 may be passed from the reactor 202 to the catalyst separation section 210. The reactor effluent 514 may include at least catalyst, reaction products, and unreacted reactants from the chemical feed, but may also include by-products, intermediate compounds, impurities, carrier gases, or other constituents. The catalyst separation section 210 may separate the reactor effluent 514 into a gaseous effluent stream 522 and a deactivated catalyst stream 524. The gaseous effluent stream 522 may include at least reaction products and unreacted reactant gases. The deactivated catalyst stream 524 may be passed to the combustor 350 for at least a portion of the catalyst processing. In the combustor 350, the supplemental fuel stream 356 may be combusted in the presence of the deactivated catalyst stream 524 to remove coke from the catalyst, heat the catalyst, or both. Following combustion, the heated catalyst 531 may be separated from the combustion gases 534 and passed to the oxygen treatment zone 370. In the oxygen treatment zone 370, the heated catalyst 531 may be treated with an oxygen-containing gas 533 to produce the reactivated catalyst 532. The reactivated catalyst 532 may then be passed back to the reactor 202.

Referring still to FIG. 2, the gaseous effluent stream 522 may be passed to the product separator 540, which may be operable to separate the gaseous effluent stream 522 into at least one product stream 542 and at least one off-gas stream 544. The off-gas stream 544 recovered from the product separator 540 of the FCDh process 502 may include at least 40 mol %, at least 70 mol %, at least 75 mol %, at least 80 mol %, at least 85 mol %, or even at least 90 mol % hydrogen based on the total molar flow rate of combustible constituents in the off-gas stream 544. The off-gas stream 544 may also include methane, nitrogen, and/or other constituents. At least a portion of the off-gas stream 544 recovered from the product separator 540 may be passed to the combustor 350 as at least a portion of the supplemental fuel stream 356. In some embodiments, the off-gas stream 544 may be combined with a secondary fuel stream 358 to produce the supplemental fuel stream 356. In some embodiments, the secondary fuel stream 358 may be a hydrogen-containing stream having a greater concentration of hydrogen than the off-gas stream 544. In other embodiments, the secondary fuel stream 358 may be a hydrocarbon stream comprising one or more hydrocarbons, such as methane or natural gas for example. In some embodiments, the flow rate of the secondary fuel stream 358, the flow rate of the off-gas stream 544, or both may be increased or decreased to change the composition (e.g., hydrogen concentration) of the supplemental fuel stream 356.

Figure 3:
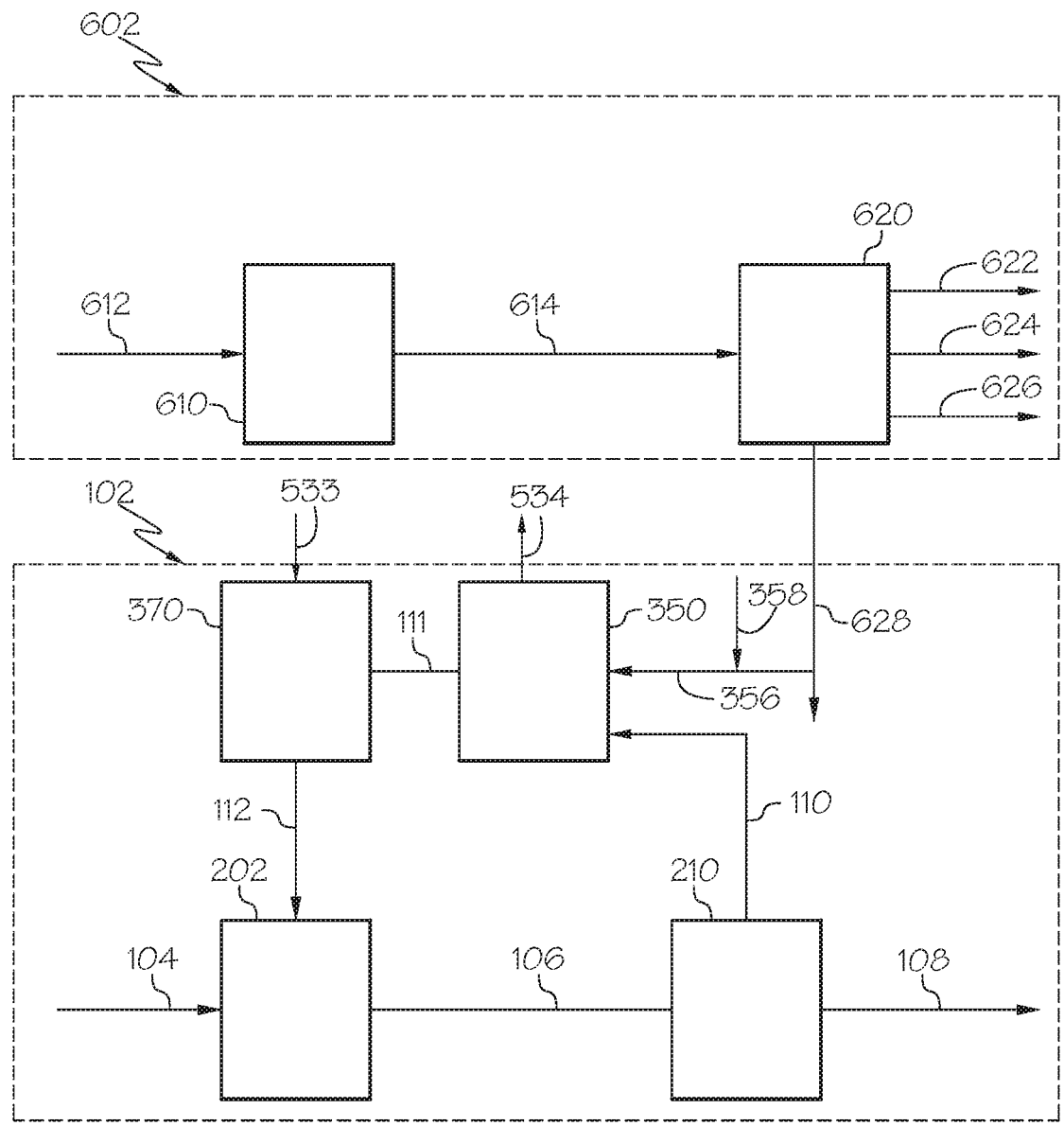
FIG. 3 schematically depicts another reactor system flow chart, according to one or more embodiments described herein.

Referring now to FIG. 3, a process flowchart depicts an embodiment in which a cracker off-gas stream 628 from a light hydrocarbon cracking process 602 may be passed to the combustor 350 of the reactor system 102 as at least a portion of the supplemental fuel stream 356. As previously discussed, the reactor system 102 can include the reactor 202, the catalyst separation section 210, the combustor 350, and the oxygen treatment zone 370. In continuous operation, a chemical feed 104 and a reactivated catalyst 112 from the oxygen treatment zone 370 may be introduced to the reactor 202, in which contact of the reactivated catalyst 112 with reactants in the chemical feed 104 may convert at least a portion of reactants in the chemical feed 512 to one or more reaction products. A reactor effluent 106 may be passed from the reactor 202 to the catalyst separation section 210, in which the reactor effluent 106 may be separated into a gaseous effluent stream 108 and a deactivated catalyst stream 110. The gaseous effluent stream 108, which may include at least one reaction product, may be passed to one or more downstream operations for further processing. The deactivated catalyst stream 110 may be passed to the combustor 350 for at least a portion of the catalyst processing. In the combustor 350, the supplemental fuel stream 356 may be combusted in the presence of the deactivated catalyst stream 110 to remove coke from the catalyst, heat the catalyst, or both. Following combustion, the heated catalyst 111 may be separated from the combustion gases 534 and passed from the combustor 350 to the oxygen treatment zone 370. In the oxygen treatment zone 370, the heated catalyst 111 may be treated with an oxygen-containing gas 533 to produce the reactivated catalyst 112. The reactivated catalyst 112 may then be passed back to the reactor 202.

Referring still to FIG. 3, the light hydrocarbon cracking process 602 may include a light hydrocarbon cracking unit 610 and a light hydrocarbon processing portion 620. During continuous operation of the light hydrocarbon cracking process 602, one or a plurality of light hydrocarbon streams 612 may be introduced to the light hydrocarbon cracking unit 610, in which light hydrocarbons in the hydrocarbon streams 612 are cracked to produce a cracker effluent 614 that includes one or more reaction products. For example, in some embodiments, the light hydrocarbon cracking unit 610 may be a steam cracker and the light hydrocarbon streams 612 may include ethane and propane, which may be steam cracked in the steam cracker to produce at least ethylene. The cracker effluent 614 may be passed to the light hydrocarbon processing portion 620 of the light hydrocarbon cracking process 602. The light hydrocarbon processing portion 620 may include a plurality of unit operations, such as but not limited to vapor compression, separation, sulfur and carbon dioxide removal, drying, or other operations. The light hydrocarbon processing portion 620 may ultimately separate the cracker effluent 614 into a plurality of gaseous streams, such as but not limited to, an ethylene product stream 622, a propylene product stream 624, a propane stream 626, a cracker off-gas stream 628, and other streams.

The cracker off-gas stream 628 may include at least 40 mol % hydrogen, such as from 50 mol % to 90 mol % hydrogen based on the total molar flow rate of combustible constituents in the cracker off-gas stream 628. At least a portion of the cracker off-gas stream 628 may be passed to the combustor 350 of the reactor system 102 to be included as a portion of the supplemental fuel stream 356. For example, in some embodiments, the cracker off-gas stream 628 may be passed directly to the combustor 350 of the reactor system 102 as the supplemental fuel stream 356 so that the supplemental fuel stream 356 consists of or consists essentially of the cracker off-gas stream 628. In some embodiments, the cracker off-gas stream 628 may be combined with a secondary fuel stream 358 to produce the supplemental fuel stream 356. The secondary fuel stream 358 may be a hydrogen-containing stream having a greater concentration of hydrogen than the cracker off-gas stream 628. Alternatively, in some embodiments, the secondary fuel stream 358 may be a hydrocarbon stream comprising one or more hydrocarbons. In some embodiments, the flow rate of the secondary fuel stream 358, the flow rate of the cracker off-gas stream 628, or both may be increased or decreased to modify the composition (e.g., hydrogen concentration) of the supplemental fuel stream 356.

In some embodiments, at least a portion of the cracker off-gas stream 628 may be combined with an off-gas stream from the reactor system 102 (e.g., off-gas stream 544 from the FCDh process 502 of FIG. 2) to produce the supplemental fuel stream 356. The supplemental fuel stream 356 may include off-gas streams from other hydrocarbon processes. In some embodiments, the supplemental fuel stream 356 may include at least one of an off-gas from an FCDh process, a cracker off-gas from a light hydrocarbon cracking unit, a purity hydrogen stream, or combinations of these.

In some embodiments, the reactor system 102 and the light hydrocarbon cracking process 602 may be integrated together to combine separation of the product streams into a single system. For example, in some embodiments, the gaseous effluent stream 108 from the reactor system 102 may be combined with the cracker effluent 614 from the light hydrocarbon cracking unit 610, and the combined effluent stream (not shown) may be passed to the light hydrocarbon processing portion 620. Thus, in these embodiments, the light hydrocarbon processing portion 620 may separate the combined effluent stream (e.g., the combination of both the gaseous effluent stream 108 and cracker effluent 614) into a plurality of gaseous streams, such as but not limited to, the ethylene product stream 622, the propylene product stream 624, the propane stream 626, the cracker off-gas stream 628, and other streams. In particular, in some embodiments, the gaseous effluent stream 522 (FIG. 2) from the FCDh process 502 (FIG. 2) may be combined with the cracker effluent 614 of the light hydrocarbon cracking process and may be passed therewith to the light hydrocarbon processing portion 620 of the light hydrocarbon cracking process 602 so that the cracker off-gas stream 628 includes off-gases produced from the light hydrocarbon cracking unit 610 and the FCDh process 502 (FIG. 2).

Figure 4:
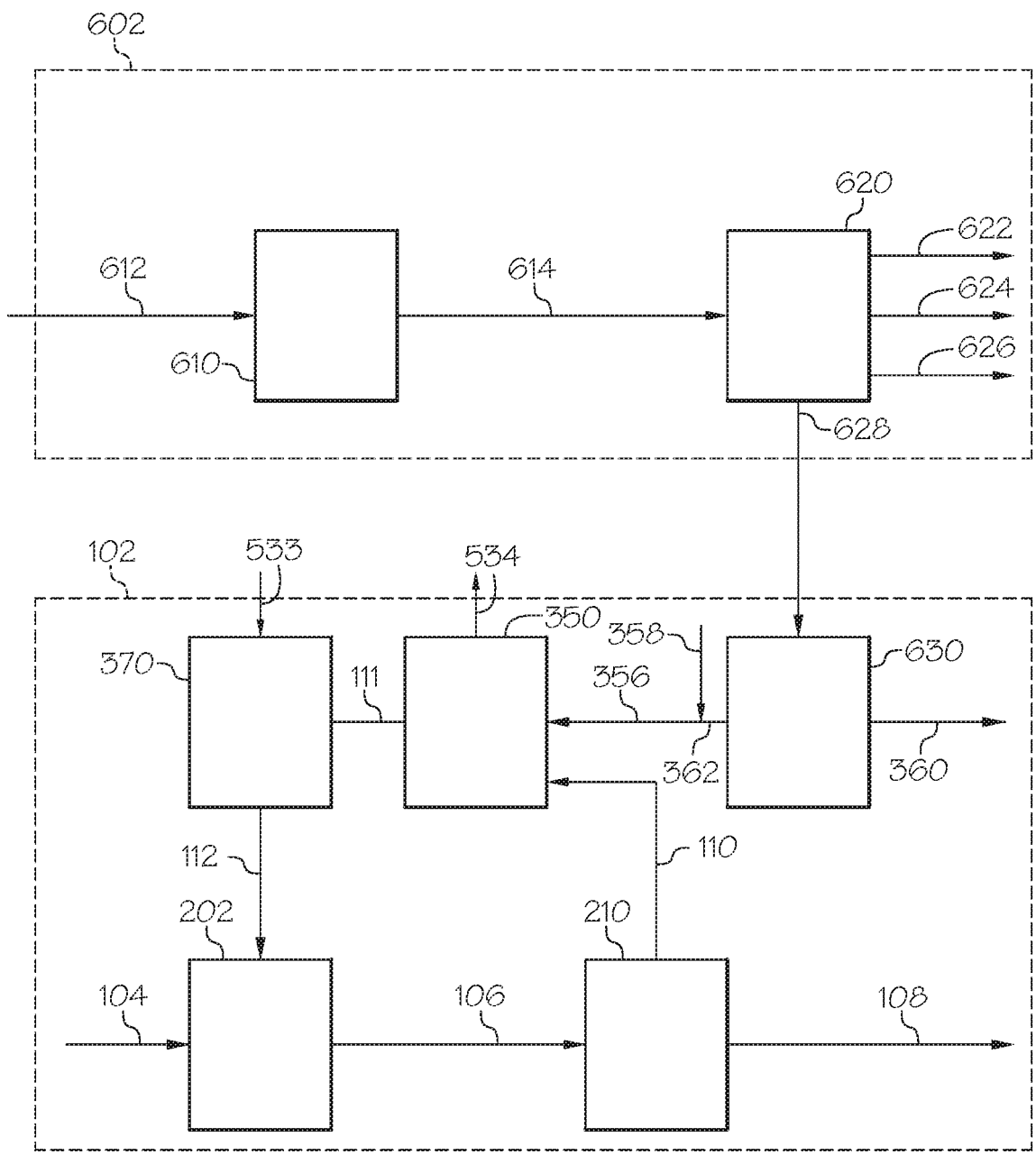
FIG. 4 schematically depicts yet another reactor system flow chart, according to one or more embodiments described herein.

Referring to FIG. 4, in some embodiments, the cracker off-gas stream 628 may be passed to a separator device 630, such as a turbo expander or other separation device. The separator device 630 may be operable to separate the cracker off-gas stream 628 into a hydrogen-rich stream 362 and a hydrocarbon-rich stream 360. The hydrogen-rich stream 362 may be passed from the separator device 630 to the combustor 350 of the reactor system 102 as at least a portion of the supplemental fuel stream 356. The supplemental fuel stream 356 may include the hydrogen-rich stream 362 from the separator device 630. Off-gas streams from other hydrocarbon processing systems (e.g., off-gas stream 544 from the FCDh process 502 of FIG. 2) may also be passed to a separator device 630 to produce a hydrogen-rich stream and a hydrocarbon-rich stream and then passing at least the hydrogen-rich stream to the combustor 350 of the reactor system 102 as a part of the supplemental fuel stream 356. In some embodiments, the operating parameters of the separator device 630 may be modified to increase or decrease a concentration of hydrogen in the hydrogen-rich stream 362 to thereby increase or decrease the concentration of hydrogen in the supplemental fuel stream 356.

In some embodiments, the hydrogen concentration of the supplemental fuel stream 356 may be modified by removing at least a portion of the hydrocarbon component from the supplemental fuel stream 356. Additionally, in some embodiments, the hydrogen concentration of the supplemental fuel stream 356 may be modified by combining the supplemental fuel stream 356 with a supplemental hydrogen-containing stream, a supplemental hydrocarbon stream, or both.

During continuous reaction phase of operation of the reactor system 102, the catalyst processing portion 300 of the reactor system 102, in particular the combustor 350, may be maintained at a temperature in an operating temperature range sufficient to reactivate the catalyst. For example, in some embodiments, the combustor 350 may be maintained at a temperature greater than the operating temperature of the reactor portion 200 of the reactor system 102. In some embodiments, the operating temperature range of the combustor 350 may be greater than or equal to 650° C., greater than or equal to 660° C., even greater than or equal to 680° C., or even greater than or equal to 700° C. In some embodiments, the operating temperature range of the combustor 350 may be from 650° C. to 850° C., from 660° C. to 780° C., or from 700° C. to 750° C. As previous discussed herein, maintaining the operating temperature in the combustor 350 may include combusting a supplemental fuel in the combustor 350. As previous discussed herein, maintaining the operating temperature in the combustor 350 may include combusting a supplemental fuel in the combustor 350.

Referring again to FIG. 1, the supplemental fuel stream 356 may be introduced to the combustor 350 of the catalyst processing portion 300. In some embodiments, the supplemental fuel stream 356 may be introduced to the combustor 350 through one or more distributors (not shown) disposed within the combustor 350. Before introducing the supplemental fuel stream 356 to the combustor 350, the supplemental fuel stream 356 may be passed through a compressor (not shown) to increase the pressure of the supplemental fuel stream 356. The supplemental fuel stream 356 can be supplied to the combustor 350 at a pressure of from 5 pounds per square inch gauge (psig) to 200 psig (from 34.47 kilopascals (kPa) to 1378.95 kPa, where 1 psig=6.89 kPa). In some embodiments, a control valve (not shown) may be included to control the flow rate of the supplemental fuel stream 356 and adjust the pressure of the supplemental fuel gas to equal the operating pressure of the reactor system 102 and/or the combustor 350. In some embodiments, the supplemental fuel stream 356 may be preheated, such as by passing the supplemental fuel stream 356 through an optional heat exchanger (not shown).

According to one or more embodiments, the reaction in the reactor system 102 may be an FCDh reaction system for dehydrogenating paraffins and alkyl aromatics to olefins or other products. According to such embodiments, the feed stream may comprise paraffinic compounds such as one or more of ethane, propane, n-butane, i-butane. In some embodiments, the feed stream may include at least 50 wt. % ethane, propane, n-butane, i-butane, or combinations thereof. In one or more embodiments, a dehydrogenation reaction may utilize a catalyst that includes platinum, gallium, or combinations thereof. The platinum and/or gallium may be carried by an alumina or alumina silica support, and may optionally comprise potassium. Such platinum catalysts are disclosed in U.S. Pat. No. 8,669,406, which is incorporated herein by reference in its entirety. In some embodiments, the reactor system 102 may be an FCDh reaction system for dehydrogenating alkyl aromatic compounds to other products. For example, the feed stream may include ethylbenzene and the reactor system 102 may be an FCDh reactor system for dehydrogenating the ethylbenzene to styrene.

In some embodiments, the reaction in the reactor system 102 may be a cracking reaction such that the reactor system 102 is a cracking reactor system. According to such embodiments, the feed stream may comprise one or more of naphtha, n-butane, or i-butane. For example, if the reaction is a cracking reaction, the feed stream may include at least 50 wt. % naphtha, n-butane, i-butane, or combinations thereof. In one or more embodiments, a cracking reaction may utilize one or more zeolites as a catalyst. In some embodiments, the one or more zeolites utilized in the cracking reaction may comprise a ZSM-5 zeolite. However, it should be understood that other suitable catalysts may be utilized to perform the cracking reaction. In some embodiments, the cracking catalyst may include platinum. For example, the cracking catalyst may include from 0.001 wt. % to 0.05 wt. % of platinum. The platinum may be sprayed on as a soluble platinum compound, such as but not limited to platinum nitrate, platinum tetraamine nitrate, platinum acetylacetonate, or combinations of these, and calcined at an elevated temperature, such as around 700° C.

EXAMPLES

Embodiments of the present disclosure will be further clarified by the following examples.

Example 1: Propane Dehydrogenation—Effects of Hydrogen Content of Supplemental Fuel on Propane Conversion In Example 1, the effects of the concentration of hydrogen in the supplemental fuel stream on the conversion of propane in the propane dehydrogenation reactor system were evaluated. The propane dehydrogenation reactions were conducted using a Davidson Circulating Riser (DCR) pilot plant unit obtained from Grace Davidson and having an upflow fluidized reactor portion and a catalyst processing portion. The DCR unit was modified to allow in-situ fuel combustion in the catalyst processing portion. Each reaction run 1A-1D was conducted with 4100 grams of freshly loaded catalyst comprising platinum and gallium supported on an alumina-containing silica carrier. The inlet temperature to the riser reactor of the DCR unit was controlled at 630° C. and the pressure was set to 13 psig. The propane feed was an HD-5 propane feed with around 30 parts per million (ppm) sulfur on a molar basis. The propane feed was diluted in nitrogen so that the partial pressure of propane in the feed stream was about 4.3 psig.

The temperature for catalyst processing was maintained in a range of from 700° C. to 750° C. Catalyst processing included combustion of a supplemental fuel stream followed by an oxygen treatment in which the catalyst was exposed to an oxygen-containing gas (air) for an oxygen soak time. The propane dehydrogenation reactions were conducted using supplemental fuel streams comprising various compositions of hydrogen and methane for the catalyst reactivation. For reaction runs 1A-1D, the molar concentration of hydrogen in the supplemental fuel stream was increased from 0 mol % hydrogen to 100 mol % hydrogen to change the molar ratio of hydrogen to methane in the supplemental fuel. The propane dehydrogenation reactions were conducted at constant heat input of about 1,600 BTU/hour (1.6 KBTU/hr). For each reaction run, the DCR unit was operated for a first period with an oxygen soak time of 1 minute and for a second period with an oxygen soak time of 7 minutes.

The propane feed rate (standard liters per hour (SLPH)), catalyst circulation rate (kg/hr), supplemental fuel stream composition (mol % and wt. %), supplemental fuel stream feed rate (SLPH), heat input (MBTU/hr), ratio of catalyst to methane (lbs/lbs) in the catalyst processing portion, propane weight hourly space velocity (WHSV $hr^{-1}$), and oxygen soak time of the oxygen treatment are provided below in Table 1. The propane conversions for operation of the reactor system with oxygen soak times of 1 minute and 7 minutes were determined and reported in Table 1.

TABLE 1

Example 1 Process Parameters and Propane Conversion

| Reaction Run | 1A | 1B | 1C | 1D |
|---|---|---|---|---|
| Supplemental Fuel Composition | | | | |
| Methane Concentration (mol %) | 100 | 75 | 20 | 0 |
| Hydrogen Concentration (mol %) | 0 | 25 | 80 | 100 |
| Molar Ratio $H_2:CH_4$ | 0:100 | 1:3 | 4:1 | 100:0 |
| Methane Content (wt. %) | 100 | 96 | 67 | 0 |
| Hydrogen Content (wt. %) | 0 | 4 | 33 | 100 |
| Reaction Process Parameters | | | | |
| Propane Feed Rate (SLPH) | 180 | 180 | 180 | 180 |
| Propane WHSV ($hr^{-1}$) | 4.5 | 4.4 | 3.6 | 3.7 |
| Catalyst Circulation Rate (kg/hr) | 18.6 | 19.5 | 20.2 | 19.5 |
| Supplemental Fuel Rate (SLPH) | 50 | 61 | 113 | 164 |
| Heat Input (KBTU/hr) | 1.57 | 1.58 | 1.56 | 1.54 |
| Propane Conversion | | | | |
| Propane Conversion (%)-oxygen soak time of 1 minute | 42.1 | 42.9 | 45.7 | 48.2 |
| Propane Conversion (%)-oxygen soak time of 7 minutes | 43.2 | 43.9 | 45.8 | 49.1 |

As shown in Table 1, for Example 1, when the molar concentration of hydrogen in the supplemental fuel is increased from 0 mol % to 100 mol % (increasing the molar ratio of hydrogen to methane in the supplemental fuel from 0:100 to 100:0), the propane conversion with an oxygen soak time of 1 minute is observed to increase from 42.1% to 48.2%. Thus, increasing the concentration of hydrogen in the supplemental fuel stream from 0 mol % to 100 mol % increased the propane conversion by 14.5%.

Example 2: Propane Dehydrogenation—Effect of Hydrogen Content of Supplemental Fuel on Propane Conversion at High Heat Input In Example 2, the effects of hydrogen concentration of the supplemental fuel stream on propane conversion in a propane dehydrogenation reactor system operating at high heat input were valuated. The propane dehydrogenation reactions were conducted in the DCR unit described in Example 1. In Example 2, the catalyst processing was conducted at high heat input which was accomplished by increasing the supplemental fuel stream flow rate to 3 times the supplemental fuel stream flow rate of Example 1. The propane dehydrogenation reactions were conducted at constant heat input of about 4,700 BTU/hour (4.7 KBTU/hr). All other operating parameters were the same. The propane dehydrogenation reactions were conducted using supplemental fuel streams comprising hydrogen and methane. For reaction runs 2A-2D, the molar concentration of hydrogen in the supplemental fuel stream was increased from 0 mol % hydrogen to 100 mol % hydrogen. The propane feed rate, catalyst circulation rate, supplemental fuel stream composition, supplemental fuel stream feed rate, heat input, ratio of catalyst to methane in the catalyst processing portion of the reaction system, propane WHSV, and oxygen soak time of the oxygen treatment are provided below in Table 2. The propane conversions for operation of the reactor system with oxygen soak times of 1 minute and 7 minutes were determined and reported in Table 1.

TABLE 2

Example 2 Process Parameters and Propane Conversion

| Reaction Run | 2A | 2B | 2C | 2D |
|---|---|---|---|---|
| Supplemental Fuel Composition | | | | |
| Methane Concentration (mol %) | 100 | 75 | 20 | 0 |
| Hydrogen Concentration (mol %) | 0 | 25 | 80 | 100 |
| Molar Ratio $H_2:CH_4$ | 0:100 | 1:3 | 4:1 | 100:0 |
| Methane Content (wt. %) | 100 | 96 | 67 | 0 |
| Hydrogen Content (wt. %) | 0 | 4 | 33 | 100 |
| Reaction Process Parameters | | | | |
| Propane Feed Rate (SLPH) | 180 | 180 | 180 | 180 |
| Propane WHSV ($hr^{-1}$) | 5.4 | 3.7 | 3.2 | 3.8 |
| Catalyst Circulation Rate (kg/hr) | 18.0 | 20.0 | 20.2 | 20.1 |
| Supplemental Fuel Rate (SLPH) | 150 | 182 | 338 | 394.3 |
| Heat Input (KBTU/hr) | 4.71 | 4.72 | 4.67 | 3.71 |
| Propane Conversion | | | | |
| Propane Conversion (%)-oxygen soak time of 1 minute | 34.9 | 37.2 | 44.0 | 48.5 |
| Propane Conversion (%)-oxygen soak time of 7 minutes | 37.7 | 43.1 | 47.0 | 49.1 |

As shown in Table 2, for Example 2, when the molar concentration of hydrogen in the supplemental fuel is increased from 0 mol % to 100 mol % (increase the molar ratio of hydrogen to methane in the supplemental fuel from 0:100 to 100:0), the propane conversion with an oxygen soak time of 1 minute is observed to increase from 34.9% to 48.5%. At high heat input (3 times the supplemental fuel stream feed rate of Example 1), the increase in propane conversion in Example 2 was 39% by increasing the hydrogen concentration in the supplemental fuel from 0 mol % to 100 mol %. Thus, at high heat input, increasing the hydrogen concentration in the supplemental fuel stream results in a greater increase in the propane conversion compared to Example 1, for which the heat input was less.

Figure 5:
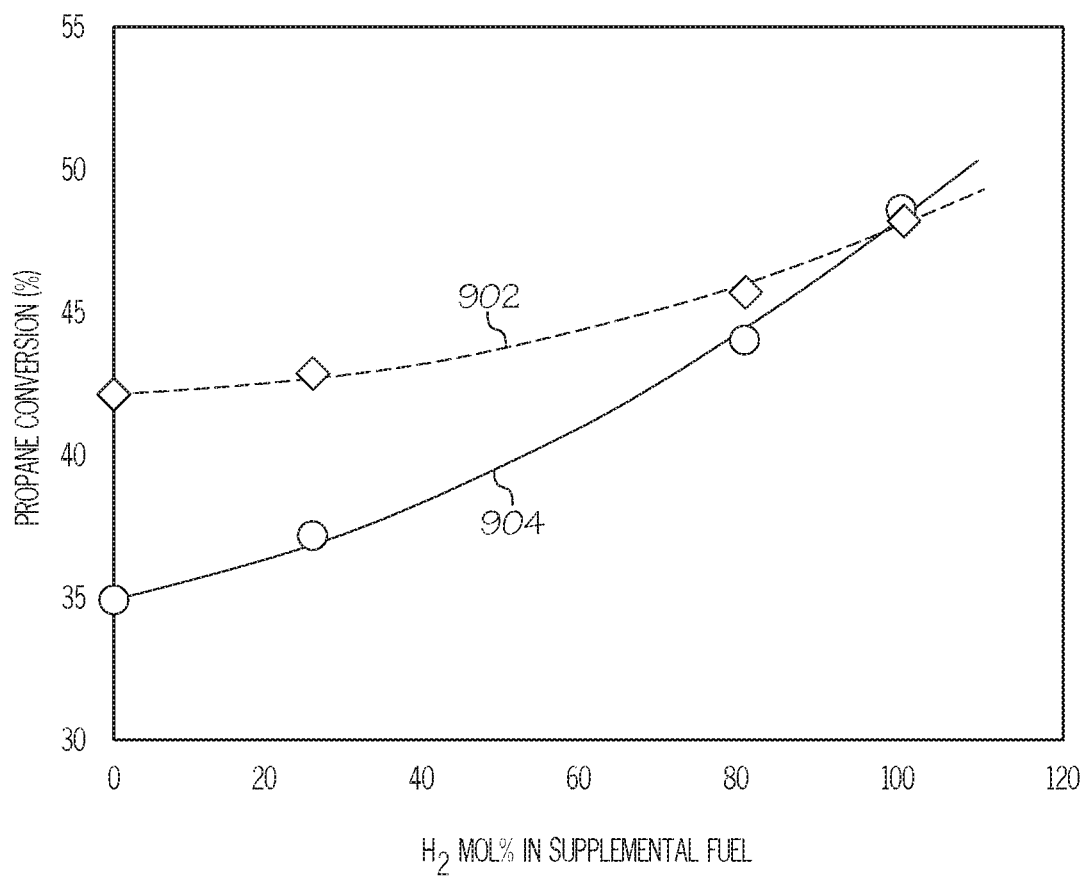
FIG. 5 schematically depicts a graph of propane conversion (y-axis) for a fluidized catalytic dehydrogenation reactor system as a function of hydrogen composition (x-axis) of a supplemental fuel introduced to a combustor of the fluidized catalytic dehydrogenation reactor system, according to one or more embodiments described herein.

Referring to FIG. 5, propane conversion (%) (y-axis) as a function of the hydrogen concentration (wt. %) in the supplemental fuel stream (x-axis) is provided for the propane dehydrogenation reactions of Example 1 (902) and Example 2 (904) with an oxygen soak time of 1 minutes. As shown graphically in FIG. 5, the propane conversion increases as the concentration of hydrogen in the supplemental fuel increases given that the total heat input to the reactor system is held constant. The increase in propane conversion is more gradual for hydrogen concentrations in the supplemental fuel of from 0 mol % to about 50 mol %. When the concentration of hydrogen in the supplemental fuel is increased to greater than 50 mol %, the rate at which the propane conversion increases with increasing concentration of hydrogen in the supplemental fuel become more rapid. This indicates a supplemental fuel that contains at least 50 mol % hydrogen (i.e., a molar ratio of hydrogen to other combustible fuels of at least 1:1) provides a considerable improvement in the propane conversion compared to a supplemental fuels having a molar ratio of hydrogen to other combustible fuels of less than 1:1. The same trend of propane conversion as a function of hydrogen concentration in the supplemental fuel stream is observed when the oxygen soak time is increased to 7 minutes.

FIG. 5 also graphically shows that the effect of the hydrogen concentration in the supplemental fuel stream on propane conversion is greater for operation at high heat input (Example 2 (904)) compared to the propane conversion for operation at lower heat input (Example 1 (902)).

Example 3: Lab Scale Propane Dehydrogenation—Effects of Hydrogen Concentration in the Supplemental Fuel Stream In Example 3, the effects of changing the hydrogen concentration in the supplemental fuel stream on the propane conversion was further studied using a lab scale propane dehydrogenation reactor system. The propane dehydrogenation reactions of Example 3 were conducted using a lab scale fixed bed testing rig containing the same catalyst previously described in Example 1. The fixed bed reactor system was alternated between propane dehydrogenation operation and catalyst reactivation to simulate reaction/catalyst processing cycles.

During propane dehydrogenation reaction operation, a feed stream comprising 90 mol % propane and 10 mol % nitrogen was introduced to the fixed bed reactor at a propane weight hourly space velocity (WHSV) of 10 hr$^{-1}$. The propane dehydrogenation reactions were conducted at a reaction temperature of 625° C. at ambient pressure. Each reaction step of the dehydrogenation/catalyst processing cycles in Example 3 was conducted for a total on-stream-time of 60 seconds, with the propane conversion and selectivity data measured 30 seconds after introducing the feed stream to the fixed bed reactor.

During each catalyst processing step of the dehydrogenation/catalyst processing cycles, a combustion gas mixture comprising a supplemental fuel stream and air was introduced to the fixed bed reactor at 730° C. for 3 minutes. The combustion gas mixture included 2.5 mol % of the supplemental fuel stream and the balance of the combustion gas mixture was air. The composition of the supplemental fuel stream consisted of methane ($CH_4$) and hydrogen ($H_2$), and the concentration of hydrogen in the supplemental fuel stream was increased from 0 wt. % to 100 wt. % in reaction runs 3A-3F. Following combustion for 3 minutes, the catalyst in the fixed bed was subjected to air treatment with high purity air (>99% air) at 730° C. for 15 minutes.

Table 3 provides propane conversion and propylene selectivity for the propane dehydrogenation reactions conducted in reaction runs 3A-3F. The propane conversion and propane selectivity in Table 3 for each of reaction runs 3A-3F were determined after the performance reached steady state (typically 20-25 reaction/catalyst processing cycles under the designated conditions in the reactor system).

TABLE 3

Propane Conversion and Propylene Selectivity for Propane Dehydrogenations of Example 3

| Rxn Run | Supplemental Fuel Stream Composition | | | Propane Conversion (%) | Propylene Selectivity (mol %) |
|---|---|---|---|---|---|
| | $CH_4$ (mol %) | $H_2$ (mol %) | Molar Ratio $H_2$:$CH_4$ | | |
| 3A | 100 | 0 | 0:100 | 48.2 | 96.4 |
| 3B | 75 | 25 | 1:3 | 48.8 | 96.5 |
| 3C | 50 | 50 | 1:1 | 50.0 | 96.6 |
| 3D | 20 | 80 | 4:1 | 50.9 | 96.6 |
| 3E | 10 | 90 | 9:1 | 51.2 | 96.6 |
| 3F | 0 | 100 | 100:0 | 53.1 | 96.8 |

As shown above in Table 3, for Example 3, when the concentration of hydrogen in the supplemental fuel was increased from 0 mol % to 100 mol % (increase in the molar ratio of hydrogen to methane in the supplemental fuel from 0:100 to 100:0), the propane conversion was observed to increase from 48.2% to 53.1%. Thus, increasing the concentration of hydrogen in the supplemental fuel stream from 0 mol % to 100 mol % increased the propane conversion by 10.2% for the lab scale reactor process of Example 3. Increasing the hydrogen concentration from 0 mol % to 100 mol % also increased the propylene selectivity from 96.4 mol % to 96.8 mol %.

Figure 6:
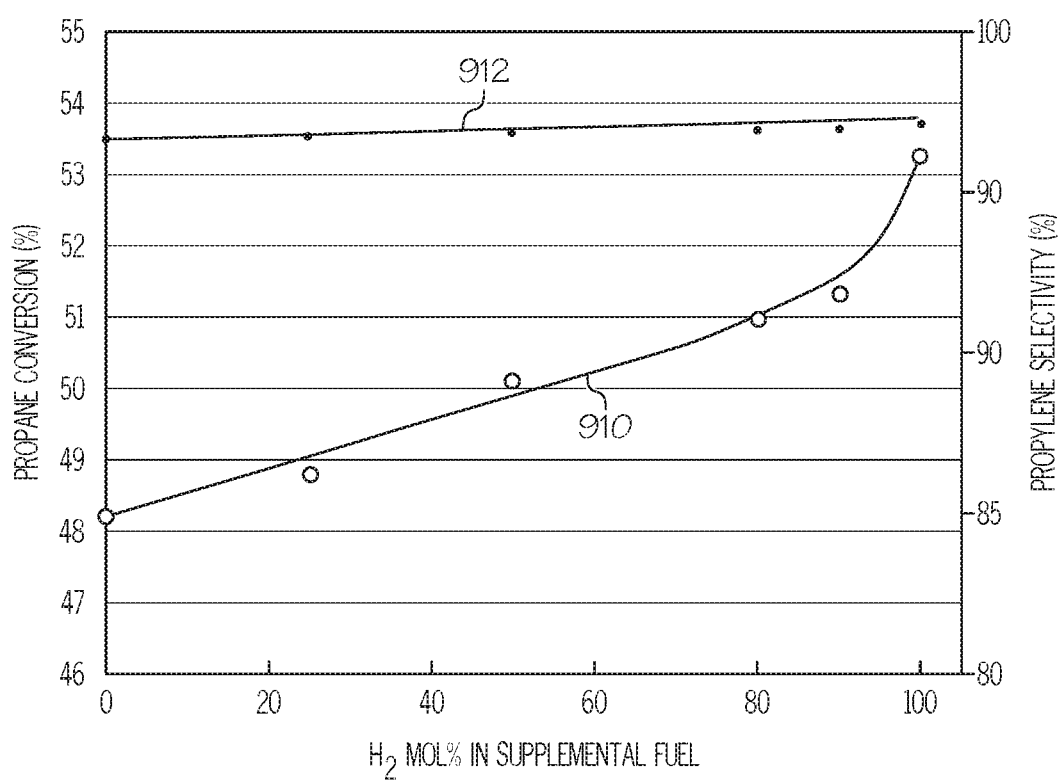
FIG. 6 schematically depicts a graph of propane conversion (y-axis left) and propylene selectivity (y-axis right) for a fluidized catalytic dehydrogenation reactor system as a function of hydrogen composition (x-axis) of a supplemental fuel introduced to a combustor of the reactor system, according to one or more embodiments described herein.

Referring to FIG. 6, propane conversion 910 (y-axis left) and propylene selectivity 912 (y-axis right) as functions of the concentration of hydrogen in the supplemental fuel stream (x-axis) are graphically depicted. As shown graphically in FIG. 6, the propane conversion 910 and propylene selectivity 912 both increase as the concentration of hydrogen in the supplemental fuel stream increases. FIG. 6 also shows that the increase in propane conversion 910 is generally linear for hydrogen concentrations in the supplemental fuel of from 0 mol % to about 70 mol %. However, when the concentration of hydrogen in the supplemental fuel stream increases above about 70 mol %, the propane conversion 910 increases more rapidly compared to the generally linear increase in propane conversion at hydrogen concentrations of from 0 mol % to about 70 mol % hydrogen in the supplemental fuel. This indicates a supplemental fuel stream that contains at least 70 mol % hydrogen provides greater improvement in the propane conversion compared to supplemental fuel streams having less than 70 mol % hydrogen.

For the purposes of describing and defining the present invention it is noted that the term "about" is utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for processing a chemical stream, the method comprising:
   contacting a feed stream with a catalyst in a reactor portion of a reactor system, wherein:
      the reactor system comprises a reactor portion and a catalyst processing portion;
      the catalyst comprises platinum, gallium, or both; and
      the contacting of the feed stream with the catalyst causes a reaction which forms an effluent stream comprising at least one product;
   separating at least a portion of the effluent stream from the catalyst;
   passing the catalyst to the catalyst processing portion of the reactor system;
   processing the catalyst in the catalyst processing portion of the reactor system, wherein processing the catalyst comprises:
      passing the catalyst to a combustor of the catalyst processing portion;
      combusting a supplemental fuel in the combustor in the presence of the catalyst to produce a heated catalyst, wherein the supplemental fuel comprises hydrogen and other combustible fuels, and a molar ratio of hydrogen to the other combustible fuels in the supplemental fuel is at least 1:1;
      treating the heated catalyst with an oxygen-containing gas to produce a reactivated catalyst; and
      passing the reactivated catalyst from the catalyst processing portion to the reactor portion.

2. A method for dehydrogenating a hydrocarbon stream to produce one or more olefins, the method comprising:
   contacting a hydrocarbon feed stream with a catalyst in a reactor portion of a reactor system, wherein:
      the reactor system comprises a reactor portion and a catalyst processing portion;
      the catalyst comprises platinum, gallium, or both; and
      the contacting of the feed stream with the catalyst causes a reaction which forms an effluent stream comprising the one or more olefins;
   separating at least a portion of the effluent stream from the catalyst;
   passing the catalyst to the catalyst processing portion of the reactor system;
   processing the catalyst in the catalyst processing portion of the reactor system, wherein processing the catalyst comprises:
      passing the catalyst to a combustor of the catalyst processing portion;
      introducing a supplemental fuel to the combustor, the supplemental fuel stream comprising hydrogen and at least one hydrocarbon, and a molar ratio of hydrogen to other combustible fuels in the supplemental fuel is at least 1:1;
      combusting the supplemental fuel in the combustor in the presence of the catalyst;
      subjecting a heated catalyst to an oxygen treatment to produce a reactivated catalyst; and
      passing the reactivated catalyst from the catalyst processing portion to the reactor portion.

3. The method of claim 1, wherein the supplemental fuel further comprises at least one hydrocarbon.

4. The method of claim 3, wherein the at least one hydrocarbon is chosen from methane, ethane, propane, n-butane, isobutane, ethylene, propylene, 1-butene, 2-butene, isobutene, pentene, benzene, toluene, xylene, natural gas, or combinations thereof.

5. The method of claim 3, wherein the at least one hydrocarbon comprises methane.

6. The method of claim 1, wherein a molar ratio of hydrogen to other combustible fuels in the supplemental fuel is from 1:1 to 99:1.

7. The method of claim 1, wherein treating the heated catalyst with the oxygen-containing gas comprises exposing the heated catalyst to the oxygen-containing gas for a time period of greater than 2 minutes.

8. The method of claim 1, further comprising passing a hydrogen-containing off-gas stream from a hydrocarbon processing system to the combustor, wherein at least a portion of a supplemental fuel stream introduced to the combustor comprises the hydrogen-containing off-gas stream.

9. The method of claim 8, further comprising increasing the concentration of hydrogen in the hydrogen-containing off-gas stream.

10. The method of claim 1, wherein the supplemental fuel comprises at least a portion of an off-gas stream from a light hydrocarbon cracking process or a dehydrogenation process.

11. The method of claim 1, further comprising:
   separating the effluent stream into a product stream and an off-gas stream; and
   passing at least a portion of the off-gas stream to the catalyst processing portion, wherein the supplemental fuel includes the at least a portion of the off-gas stream.

12. The method of claim 1, wherein the catalyst comprises platinum, gallium, and optionally an alkali metal or alkaline earth metal supported on a carrier, the carrier chosen from one or more of silica, alumina, alumina-containing silica, $TiO_2$, $ZrO_2$, or combinations thereof.

13. The method of claim 1, wherein the reactor system comprises a dehydrogenation reaction system.

14. The method of claim 1, wherein the product in the effluent stream comprises at least one light olefin chosen from ethylene, propylene, or butene.

15. The method of claim 1, further comprising operating the combustor at a temperature of from 650° C. to 850° C.

16. The method of claim 2, wherein:
   the supplemental fuel further comprises at least one hydrocarbon; and
   the at least one hydrocarbon is chosen from methane, ethane, propane, n-butane, isobutane, ethylene, propylene, 1-butene, 2-butene, isobutene, pentene, benzene, toluene, xylene, natural gas, or combinations thereof.

17. The method of claim 2, wherein a molar ratio of hydrogen to other combustible fuels in the supplemental fuel is from 1:1 to 99:1.

18. The method of claim 2, wherein the supplemental fuel comprises at least a portion of an off-gas stream from a light hydrocarbon cracking process or a dehydrogenation process.

19. The method of claim 2, further comprising:
   separating the effluent stream into a product stream and an off-gas stream; and
   passing at least a portion of the off-gas stream to the catalyst processing portion, wherein the supplemental fuel includes the at least a portion of the off-gas stream.

20. The method of claim 2, wherein the catalyst comprises platinum, gallium, and optionally an alkali metal or alkaline earth metal supported on a carrier, the carrier chosen from one or more of silica, alumina, alumina-containing silica, $TiO_2$, $ZrO_2$, or combinations thereof.

* * * * *